United States Patent
Hansen (10) Patent No.: US 11,419,766 B2
(45) Date of Patent: Aug. 23, 2022

(54) ANIMAL HEARING PROTECTION AND COMMUNICATION DEVICE AND METHOD OF OPERATION

(71) Applicant: Susan M. Hansen, Sedro Wooley, WA (US)

(72) Inventor: Susan M. Hansen, Sedro Wooley, WA (US)

(73) Assignee: CrittEar, LLC, Sedro Woolley, WA (US)

( * ) Notice: Subject to any disclaimer, the term of this patent is extended or adjusted under 35 U.S.C. 154(b) by 288 days.

(21) Appl. No.: 16/420,008

(22) Filed: May 22, 2019

(65) Prior Publication Data

US 2020/0368070 A1 Nov. 26, 2020

(51) Int. Cl.
*A61F 11/08* (2006.01)
*A01K 15/02* (2006.01)
*A61F 11/14* (2006.01)

(52) U.S. Cl.
CPC ............ *A61F 11/08* (2013.01); *A01K 15/021* (2013.01); *A61F 11/14* (2013.01)

(58) Field of Classification Search
CPC .... A61F 11/08; A61F 2011/085; A61F 11/10; A61F 11/00; A61F 11/06; A61F 2/0095; A61F 13/49; A61F 2002/183; A61F 2210/0014; A61F 2230/0023; A61F 2230/005; A61F 2/18; A61F 11/12; A61F 11/008; A61F 2011/145; A61F 2250/0018; A61F 2250/004; A61F 11/085; A61F 11/30; A61F 11/145; A61F 2/08; A61F 11/006; A61F 2220/0075; A61F 2230/0063; A61F 2240/002; A61F 2250/0085; A61F 11/14; H04R 2420/07; H04R 1/1016; H04R 1/028; H04R 7/127; H04R 1/1008; H04R 25/606; H04R 25/552; H04R 25/652; H04R 25/654; A01K 15/021

See application file for complete search history.

(56) References Cited

U.S. PATENT DOCUMENTS 5,917,918 A * 6/1999 Callahan ............... H04R 1/1016
381/67
6,591,786 B1 7/2003 Davis
7,506,720 B1 3/2009 Hicks
(Continued)

FOREIGN PATENT DOCUMENTS

WO WO-2006111794 A2 * 10/2006 ............. B43K 29/10

*Primary Examiner* — Ophelia A Hawthorne
(74) *Attorney, Agent, or Firm* — Harold H. Bennett, II (57) ABSTRACT

A sound-limiting device is provided, that includes an earplug body of a resilient elastomeric material, and that has a first portion whose shape corresponds generally to the shape of the vertical canal of a dog's ear canal, and a second portion sized and configured to flex through the elbow region of the dog's ear canal and into the horizontal canal. A spring element can be encapsulated in the first portion of the earplug body, and configured to apply a spring bias radially outward from an axis extending a length of the earplug body. The spring element is of a shape memory alloy having a transition temperature that is below a normal body temperature of a dog. The device can also include a sound conditioning element configured to produce a signal that is audible to an animal wearing the device.

15 Claims, 7 Drawing Sheets

(56) References Cited

U.S. PATENT DOCUMENTS

2007/0183613 A1\* 8/2007 Juneau .................... A61F 11/10
  381/322
2009/0032031 A1\* 2/2009 Goyer ...................... A61D 9/00
  128/864

\* cited by examiner

FIG. 10B

ANIMAL HEARING PROTECTION AND COMMUNICATION DEVICE AND METHOD OF OPERATION

BACKGROUND a. Field of the Invention

The present disclosure relates generally to hearing protection devices for animals, and, more particularly, to active and passive hearing protection devices for dogs.

b. Related Art

Many domesticated animals are subject to noisy environments, and in many cases to conditions that can result in hearing damage. For example, dogs and horses that are trained for use by military and police personnel are frequently present while guns are discharged, both during training and, less frequently, while working. Many hunting dogs are trained to stand close by while their handlers fire rifles or shotguns. Pet handlers frequently travel with their pets by airplane, and though perhaps not immediately harmful, the sound produced by jet engines during flight can cause significant distress for many kinds of animals. Many other examples could be provided, of situations in which pets or working animals are subjected to noises that are distracting, distressing, or harmful.

To the extent that there are products available to provide hearing protection for such animals, the products are primarily in the form of insulated earmuffs or covers designed to be placed over an animal's ears, so as to muffle ambient noise.

SUMMARY OF THE INVENTION

According to an embodiment, a sound-dampening device is provided that includes an earplug body of a resilient elastomeric material, and that has a first portion whose shape corresponds generally to the shape of the vertical canal of a dog ear, and a second portion sized and configured to flex through the elbow region of the dog ear and into the horizontal canal.

According to an embodiment, a spring element is encapsulated in the first portion of the earplug body, configured to apply a spring bias radially outward from an axis extending a length of the earplug body. The spring element is of a shape memory alloy having a transition temperature that is below a normal body temperature of a dog.

According to an embodiment, the device includes a sound conditioning element configured to produce a signal that is audible to an animal wearing the device.

According to various embodiments, the audible signal includes one or more of: a noise cancellation signal, a volume-limited transmission of ambient sounds, a wirelessly received voice signal from a handler, a click signal, a whistle signal, a tone signal, etc.

According to an embodiment, the device includes a cap element that is coupled to the earplug body.

According to an embodiment, the device is configured to be worn in the ear canal of a dog.

BRIEF DESCRIPTION OF THE DRAWINGS

FIGS. 2A-2C are respective views of an earplug for use in providing hearing protection for dogs and other animals, according to an embodiment.

DETAILED DESCRIPTION

Hearing protection devices that are currently available for animals can be very effective in providing protection from loud noises, but they also have some weaknesses and drawbacks. First, the variety of sizes and shapes of animals' heads can make it difficult to obtain earmuffs for a particular animal that fit and provide an adequate seal around the animal's ears. This can be a serious problem, inasmuch as a poor seal significantly degrades the protection, and most animals and their human owners, trainers, or handlers (hereafter, handlers) can't communicate at a level that would permit the animals to understand the need for a tight fit, or to provide the feedback necessary for their handlers to achieve such a fit. For a manufacturer, it would be prohibitively expensive to provide earmuff models for every size and shape of animal head, so a handler may not be able to find a suitable pair for a particular animal.

Even assuming an animal is provided with a well-fitted pair of earmuffs, such devices have other drawbacks. For example, in tight spaces, earmuffs can interfere with movement or snag on protruding obstacles, or an animal may intentionally remove them if they are uncomfortable or unfamiliar. The inventor has further recognized that many working animals, particularly dogs, rely on their hearing to perform their work. Many handlers provide audible commands to direct the animal, such as voice commands, whistles, or clicks, etc. If a hearing protection device interferes with such commands, the animal's performance and efficiency will suffer.

The inventor's work has focused primarily on dogs, inasmuch as they comprise the majority of working animals. Embodiments of the invention will therefore be described below as they apply to dogs. However, the inventor contemplates that the principles disclosed herein can be adapted to apply to a wide range of species of working animals and pets, including cats, horses, camels, elephants, etc. These adaptations will vary, depending upon the size and anatomy of a particular species and animal, as well as the goals or intentions of the handler. Accordingly, features of different embodiments can be combined with those of other disclosed embodiments, while other features can be omitted, to produce further embodiments. The claims are therefore not limited to specific embodiments or specific species.

One type of hearing protection that is very common for use by humans who wish to dampen ambient noise is the earplug, particularly the foam earplug, which comprises a more or less cylindrical plug of a resilient foam elastomer, which is worn inside the ear canal of the user. When not in use, such earplugs are typically about half an inch in diameter, and about an inch in length. To insert the earplug, the user first twists and/or rolls the plug into a cylindrical shape that is smaller in diameter than the ear canal, then inserts the plug therein. Over the course of a few tens of seconds, or minutes, the elastomeric plug expands back toward its original size and shape until it completely fills and conforms to the user's ear canal, providing an effective barrier to ambient sounds. The range of sizes (of ear canals) that a particular size can accommodate effectively depends upon factors such as the density, elasticity, and resiliency of the foam elastomer, while the degree of sound attenuation depends not only upon the formulation of the elastomer, but also upon the length of the plug within the ear canal.

Figure 1:
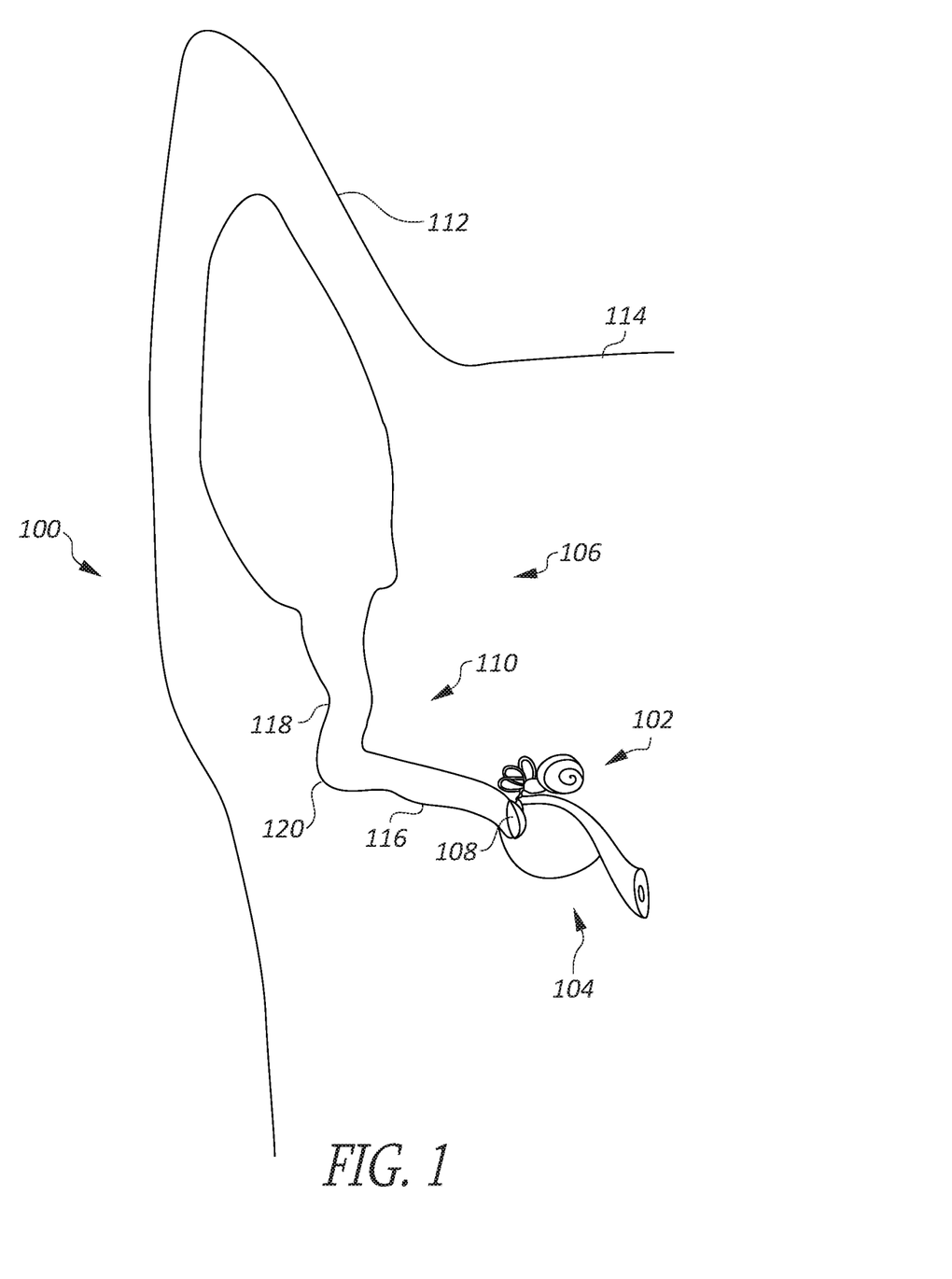
FIG. 1 is a diagram showing the typical anatomy of a dog ear.

The inventor considered the use of such earplugs in dogs, but found them to be inadequate, and not entirely adaptable for use in dogs. FIG. 1 is a diagram showing the typical anatomy of a dog ear 100. The function of the dog ear 100, i.e., the manner in which sound, in the form of pressure waves, is converted to nerve impulses in the ear of a dog, is broadly similar to the function of the human ear, and comprises analogous structures. The dog ear 100 includes the inner ear 102, the middle ear 104 and the outer ear 106, the outer ear being the portion of the ear that lies outside the tympanum 108. Embodiments described herein are directed primarily to the function of the outer ear 106 and the control of sound transmitted to the tympanum 108. The outer ear 106 includes the tympanum 108, the ear canal 110, and a pinna 112, i.e., the portion of the dog's ear that is visible outside the animal's head 114. A significant distinction is that, where the ear canal of a human ear is substantially straight or gently curved along its entire length, the ear canal 110 of a typical dog ear 100 includes a horizontal canal 116, closest to the tympanum 108, and a vertical canal 118, which joins with the horizontal canal at an elbow region 120 and extends to the pinna 112. This general structure is common to most dogs, though it varies in detail—and of course in size—according to the size and breed of the dog.

In testing various types and designs of earplugs, the inventor found that earplugs designed for use by humans were not satisfactory for use by dogs. One problem is that the vertical canal 118 has a generally conical shape, while a human ear canal is more cylindrical in shape. Thus, an earplug that was small enough to fit into the inner portion of the vertical canal 118 did not expand enough to fully conform to the outer portion of the vertical canal. Conversely, an earplug that was large enough to fully conform the outer portion was difficult to insert as far as the inner portion, and was more likely to cause discomfort. Even the use of more conically-shaped earplugs did not fully resolve the problems. Because of the conical shape of the vertical canal 118, the inventor found that, perhaps due to small movements and flexing of the surrounding tissue, an earplug had a tendency to gradually work its way out over time, so as to dislodge and fall from a dog's ear.

The inventor has found that if an earplug is able to be introduced past the elbow region 120 of the ear canal 110, that there is a much lower likelihood that the plug will work itself out of the ear 100. However, earplugs designed for use by humans are too short to reach the elbow region 120 in all but the smallest dogs, while their diameter is too large to enter the horizontal canal 116 in all but the largest dogs.

The only earplugs of which the inventor is aware that are at all adequate to provide hearing protection for dogs are custom-made for each animal, in a process in which an uncured material is injected into the animal's ears and allowed to cure in place, as described, for example, in U.S. Pat. No. 6,591,786, issued on Jul. 15, 2003, which patent is incorporated herein by reference in its entirety. Such earplugs would be prohibitively expensive for many dog owners, inconvenient for most dog owners, and require significant discipline on the part of the dog, to tolerate the formation process.

The inventor has recognized that currently available mass-produced earplugs are inadequate because they do not extend beyond the elbow region of the dog's ear canal, resulting in inferior sound dampening and a tendency to fall out. The inventor has further recognized the need for an earplug product that can be inexpensively mass-produced in a limited number of sizes to fit a majority of the dog population.

Hereafter, longitudinal, and related terms refer to dimensions, directions, and axes extending substantially parallel to the Z axis shown in the drawings, while terms such as transverse and lateral refer to dimensions, directions, and axes lying in a plane that is substantially parallel to a plane defined by the X and Y axes shown in the drawings. Other terms, such as length, width, height, etc., are used to define particular dimensions of a device along axes parallel to one or another of the X, Y, or Z axes, as described below. Terms such as top, bottom, upper, lower, etc. refer to relative positions of referenced elements as they appear in specified drawings. As used in the claims, none of the terms mentioned above are limited by the actual orientation of a physical device on which a claim reads, but only by the positions of the referenced features of the device, relative to other features of the device, as they are described below.

Figure 2A:
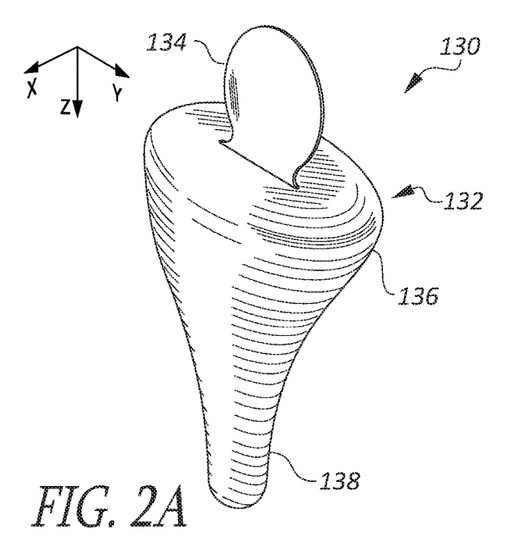
FIG. 2A is a perspective view.
Figure 2B:
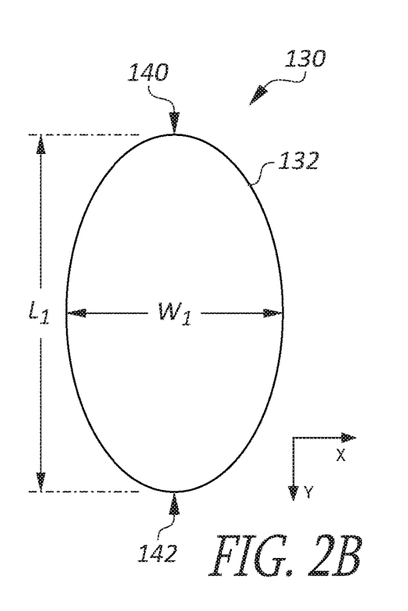
FIG. 2B is an outline in top plan view.
Figure 2C:
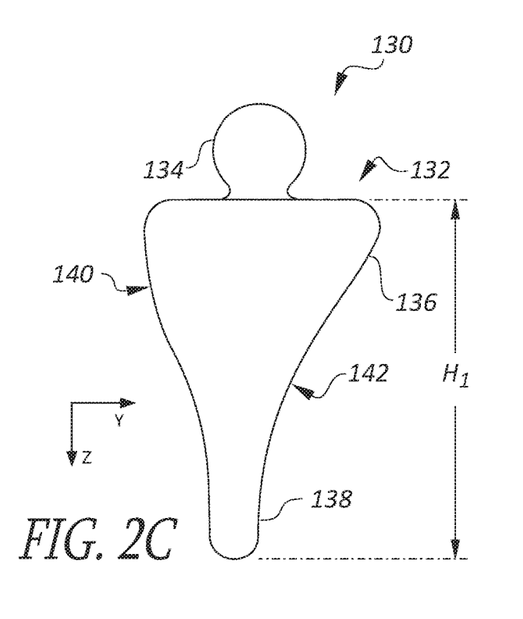
FIG. 2C is a side elevation view.

FIGS. 2A-2C are respective views of an earplug 130 for use in providing hearing protection for dogs and other animals, according to an embodiment. FIG. 2A is a perspective view, FIG. 2B is an outline in top plan view, and FIG. 2C is a side elevation view, which together disclose a shape that the inventor has found to be effective for most species of dogs, when scaled appropriately. The earplug 130 includes a body 132 of a resilient foam elastomer, and a tab 134 configured to facilitate removal of the earplug from an animal's ear. The tab 134 is of a pliable material, with a lower portion attached to the body 132 and extending out from the body. The tab 134 can be made of the same material as the body, or any appropriate material, such as nylon, polyester, Tyvek®, etc.

The body 132 includes a first portion 136 with a generally flattened conical first profile, and a second portion 138 with a generally cylindrical or more gently tapered conical second profile. According to an embodiment, the second portion 138 comprises about 5 to 50 percent of the total length of the body 132. According to another embodiment, the second portion 138 comprises about 10 to 25 percent of the total length of the body 132. According to a further embodiment, the second portion 138 comprises about 15 to 20 percent of the total length of the body 132. According to another embodiment, the second portion 138 comprises about 35 to 45 percent of the total length of the body 132.

In plan view, the first portion 136 of the earplug 130 is generally oval in shape, as shown in FIG. 2B. As best shown in FIG. 2C, the body is slightly asymmetrical, when viewed normal to a Y-Z plane, with a bulge, or swell along a front side 140, while a back side 142 curves smoothly along its length. The shape of the earplug 130, and particularly of the first portion 136, corresponds generally to the typical shape of a dog's ear canal. The oval outline of the body 132, as viewed in plan, has a length L1, front to back, of between about 1.4 and 1.7 times its width W1, and a height H1 of between about 2.3 and 2.7 times its width. The embodiment shown has a height of about 1.75 inches, a length of about 1.15. inches, and a width of about 0.7 inches. This size is effective for use in large dogs, such as, for example, German Shepherds of more than about 70 pounds. The inventor has found that about five sizes is sufficient to fit the ear canals of most species of dogs, and contemplates a commercial line of such earplugs, with one size larger than the embodiment described, and three sizes that are smaller. Other sizes have proportions that are about the same as those of the dimensions described above.

A method of inserting the earplug 130 is similar to a method described below with reference to FIGS. 3-5.

The formulation of the resilient elastomer, the length of the body 132, and the particular shapes of the profiles of the first and second portions 136, 138 are selected to enable the earplug 130 to be compressed so as to be insertable into the ear canal 110 of a dog, with the tab 134 extending into the pinna 112 and at least part of the second portion 138 extending past the elbow region 120 and into the horizontal canal 116, and to expand so as to substantially conform to the shape of the ear canal 110 along the length of the body 132. The body 132 can be any suitable elastomeric material capable of being compressed to a sufficiently small diameter as to be insertable into the ear canal 110 of a dog, and to expand to conform to the shape of the ear canal. Such suitable materials include, for example, polyurethane, silicone, natural and synthetic rubber, etc. Elastomeric materials have a number of properties that can be modified during the manufacturing process. These properties include elasticity, which is a measure of the material's ability to return to its original shape after being deformed, and also affects the ability of a material to conform to complex shapes; resiliency, which is a measure of the speed with which the material returns to its original shape after being deformed; and density, which affects the sound damping ability of the material. Materials that have relatively high elasticity with low resiliency, i.e., slow recovery times, are sometimes referred to as viscoelastic, and, in consumer application, as memory foam.

A minimum degree of correspondence of the shape of the earplug to the shape of the ear canal 110 depends upon the conformability of the elastomeric material from which it is made. I e., if the elastomeric material has a higher degree of conformability, it can be formed into a body that is less closely shaped to the shape of the ear canal. Accordingly, the claims are not limited by the sizes, shapes, or proportions described with reference to FIGS. 2A-2C, except where those limitations are explicit. Furthermore, the inventor contemplates embodiments for use with animals other than dogs, some of which will be significantly different is size, shape, and proportion than the disclosed embodiments. The inventor has observed some other problems in developing an effective earplug design. In particular, if the elastomer is not sufficiently elastic, it will not conform to the ear canal 110, and so may not provide adequate protection. Additionally, if the resiliency is too great, the body 132 may expand too quickly, making it difficult to fully insert the plug. This is particularly the case when working with a less experienced animal, which may tend to wriggle or squirm, making insertion a more lengthy process. Thus, it would be beneficial to be able to delay the expansion of at least some portions of the body 132. On the other hand, typical earplugs designed for use by humans have a relatively low resiliency, i.e., a long recovery time; they can take anywhere from around twenty seconds to more than three minutes to expand to fill the ear canal after insertion. In many dogs, the handler would find it necessary to hold the earplugs in place until they had expanded to a degree sufficient to prevent them from falling out of the dog's ears, which might be at least twenty seconds or as much as two or three minutes. Even twenty second can be a challenge with a dog that is energetic or exited. The inventor experimented with a wide range of materials and material properties, with a number of different dogs, and found that a recovery time of seven to ten seconds is an appropriate range for most dogs. This gives the handler time to insert an earplug, but does not need to hold the plug in place for an extended period. The inventor also contemplates an embodiment in which the earplug has a longer recovery time, for use with dogs that are not yet trained to hold still while earplugs are inserted, giving the handler more time to perform the process. According to an embodiment, the earplug has a recovery time of five to thirty seconds. According to an embodiment, the recovery time is between five and fifteen seconds. According to another embodiment, the recovery time is between seven and ten seconds. According to an embodiment, the recovery time is between ten and twenty seconds.

As used herein the term recovery time, when used with reference to an earplug, is the time required for an earplug, having been compressed to a volume of 15% to 25% of its uncompressed volume, to expand back to its uncompressed volume. When used with reference to the material of an earplug, recovery time refers to the time required for a two-inch cube of the material to return to its original height after having been compressed by a five-pound weight.

Figure 3:
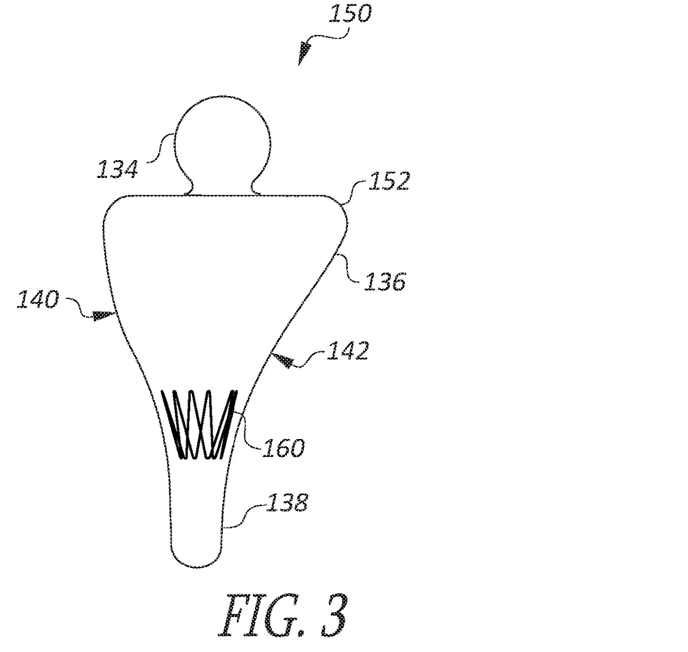
FIG. 3 is a diagrammatic side view of an earplug, according to another embodiment, that is in most respects similar to the earplug of FIGS. 2A-2C.

FIG. 3 is a diagrammatic side view of an earplug 150, according to an embodiment, that is, in most respects similar to the earplug 130 of FIGS. 2A-2C. The earplug 150, which is rendered as a transparent outline, includes a body 152 and a spring element 160 encapsulated within the body and positioned such that when the earplug 150 is properly position in the ear canal 110 of the dog ear 100, the spring element 160 is within the vertical canal 118 close to but outside the elbow region 120, and is oriented and configured to exert a spring bias radially, substantially normal to a longitudinal axis (i.e., the Z axis) of the body 152, as viewed in FIG. 3.

Figure 4:
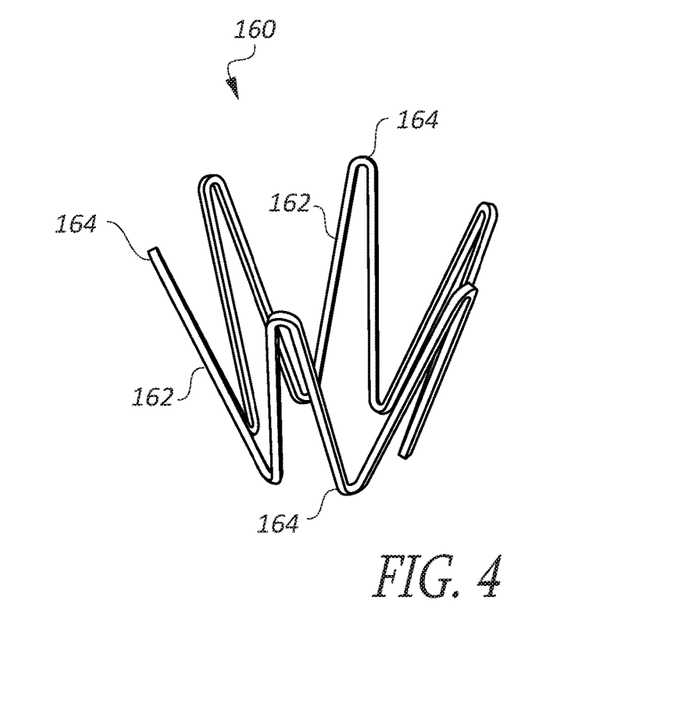
FIG. 4 is a perspective view of a spring element of the embodiment of FIG. 3.

According to an embodiment, the spring element 160, shown in more detail in FIG. 4, is made of a shape-memory alloy and includes respective pluralities of straight and bent segments 162, 164 that together form a generally conical convoluted spring form. According to another embodiment, the spring element 160 has a more cylindrical shape.

A shape-memory alloy is an alloy that transitions between a martensite phase or structure and an austenite phase or structure at a transition temperature that is very low, as compared to many alloys. While in the martensite phase, the alloy is malleable, and able to undergo significant deformation without breaking atomic bonds. However, when heated beyond its transition temperature, the alloy transforms to its austenite structure, in which it returns to its fixed, or parent shape.

The most common shape-memory alloys are nickel-titanium (Nitin) alloys and copper-aluminum-nickel (Cain) alloys. Properties of the material, such as the transition temperature, are determined by the specific ratio of the constituent elements, and sometimes also by the presence and quantities of other trace elements. The parent shape is established by holding the material in a desired shape while heating it to a fixing temperature, typically in the 900-950-degree F. range.

Assuming, for example, that the shape shown in FIG. 4 is the parent shape of the spring element 160, as long as the element is below its transition temperature, it can be easily bent or formed to assume, for example, a narrow cylindrical shape, and will remain in that shape, but when heated to its transition temperature, it will attempt to return to the shape shown in the drawing, and will behave as a spring for as long as the temperature remains above the transition temperature.

According to an embodiment, the spring element 160 is made of Nitinol® (a nitic shape-memory alloy) having a transition temperature selected to be slightly below the typical body temperature of a dog (about 101-102.5 degrees F.), such as, for example, about 90-95 degrees F. Accordingly, at room temperature, the earplug 150 can be compressed into a smaller diameter, and the spring element 160 will remain compressed, thereby holding the lower part of the first portion 136 at a reduced diameter. However, once the earplug is introduced into the ear of a dog, the animal's body heat will warm the spring element 160 until it reaches the transition temperature, whereupon the spring element will attempt to return to its parent shape, applying a resilient spring bias to the encapsulating elastomeric material of the body 152 and ultimately to the inner wall of the vertical canal 118, enhancing the security and seal of the device within the ear canal 110.

To insert the earplug 150, the handler first compresses the body 152 to a reduced diameter sufficient to be fully inserted into the ear canal of an appropriately sized dog. The handler then gently grasps and pulls the pinna 112 upward, which causes the dog's ear canal 110 to straighten, and while holding the pinna, slides the earplug into the ear canal, with the front edge 140 facing forward, i.e., more or less parallel to the dog's nose, and the back edge 142 toward the dog's tail. Once in position, the handler releases the pinna 112, while holding the earplug in place. The ear canal 110—together with the second portion 138 of the body ! 52—immediately collapses into the horizontal and vertical canals 116, 118. As the body 152 recovers back toward its normal shape, it begins to conform to the shape of the ear canal 110, so that after a few moments, it is no longer necessary to hold the plug in place. The second portion 138 extends through the elbow region 120 and into the horizontal canal 116, providing a secure engagement, and over a few minutes, the spring element 160 warms enough to transition to the austenitic phase, increasing the conformity and security of the engagement.

Figure 5:
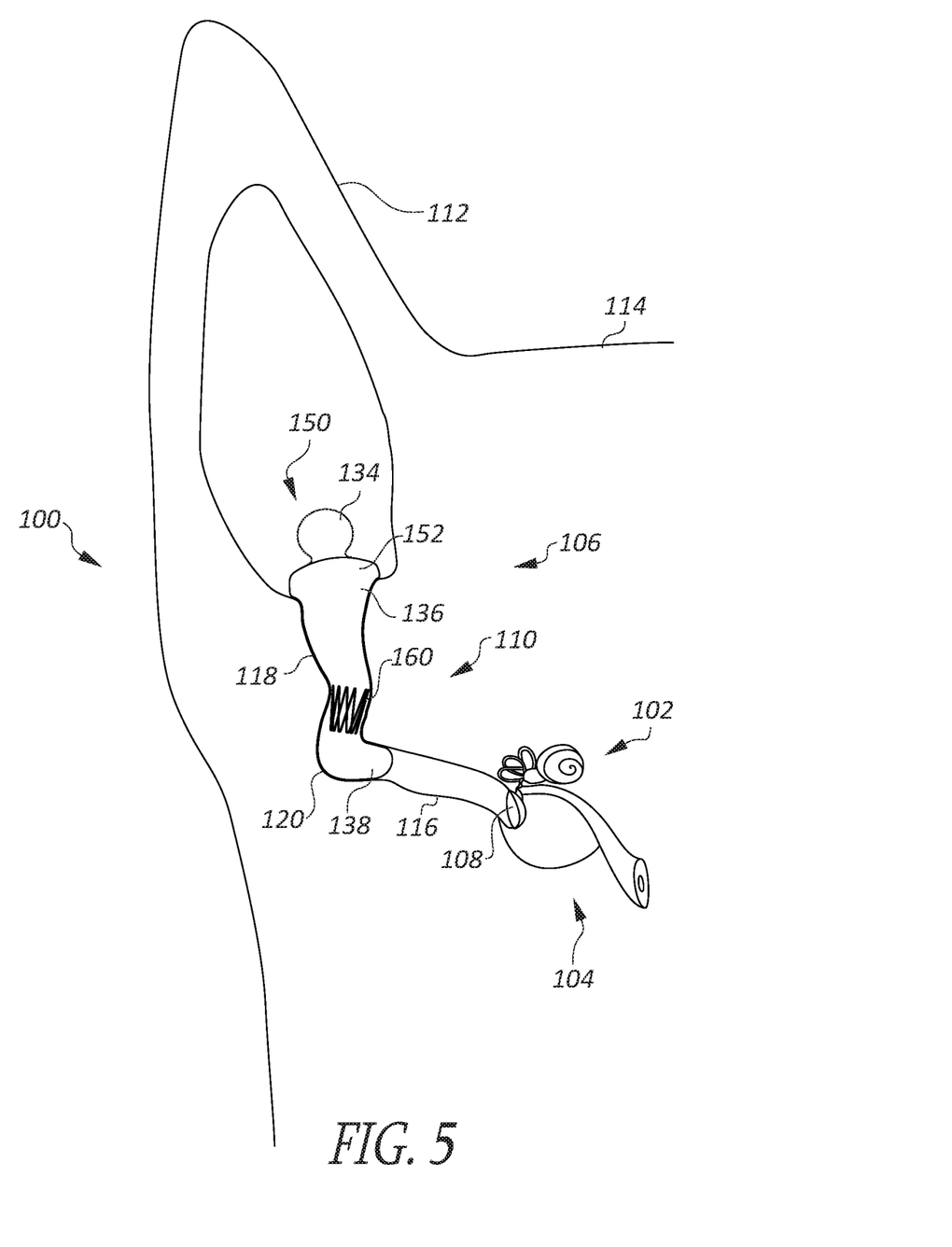
FIG. 5 is a diagram showing the earplug of FIG. 3 in place in the ear canal of the dog ear of FIG. 1, according to an embodiment.

FIG. 5 is a diagram showing the earplug 150 of FIG. 3 in place in the ear canal 110 of the dog ear 100 of FIG. 1, according to an embodiment. The body 152 extends substantially the length of the vertical canal 118, with the second portion 138 extending past the elbow region 120 and into the horizontal canal 116, with the spring element 160 positioned near the elbow region 120 in the vertical canal 118. The earplug 130 described above with reference to FIGS. 2A-2C can be inserted into the dog ear 100 using the same procedure described above for the insertion of the earplug 150.

Figure 6:
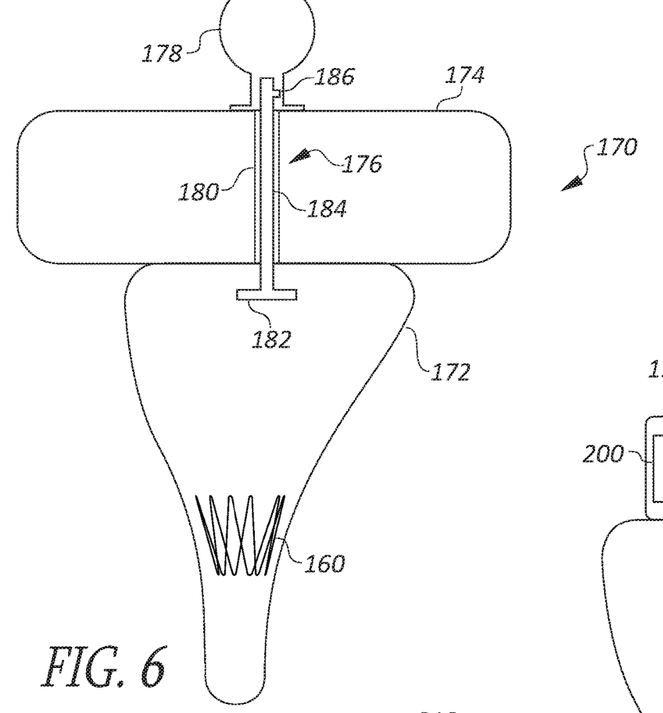
FIGS. 6, 7, and 8 are diagrammatic side elevation views of earplugs for use in providing hearing protection for dogs and other animals, according to respective additional embodiments.

FIG. 6 is an earplug 170 for use in providing hearing protection for dogs and other animals, according to an embodiment. The earplug 170 includes a body 172, a cap element 174, a locking pin 176, and a tab 178. In the embodiment shown, the cap element 174 is made of a resilient elastomeric foam or other pliable and resilient material, and has an aperture 180 extending therethrough. According to one embodiment, the cap element 174 is configured to cover the opening of the ear canal 110, enhancing the sound dampening provided by the body 172. The cap 174 is sized to fit within the pinna 112 and to conform to the lower interior of the pinna around the opening of the ear canal 110. The locking pin 176 includes a base 182 that is embedded in the material of the body 174, a shaft 184 sized and configured to extend through the aperture 180 and a locking tooth 186, configured to engage a corresponding feature of the tab 178. The locking pin 176 and tab 178 are of a rigid plastic, such as, e.g., acrylic. By rotation of the tab 178, a user can engage or disengage the cap 174 from the body 172, which permits replacement or exchange of the cap or the body as necessary. According to some embodiments, the cap 174 has a shape and/or a color selected to identify a manufacturer, a model, a size, etc., and/or to make the earplug 170 more visible.

As noted above, one drawback with various known types of hearing protection devices for animals is that they are generally indiscriminate in the dampening of sound, while many working animals, particularly dogs, rely upon their hearing to perform their tasks. For example, a police dog typically responds to voice commands from its handler to perform searches, subdue suspects, etc., but may also be nearby when its handler is discharging a firearm, both during training and in the field. The sound attenuation of a protective device can reduce the effective distance within which the handler's commands can be heard, or require the handler to speak more loudly.

Figure 7:
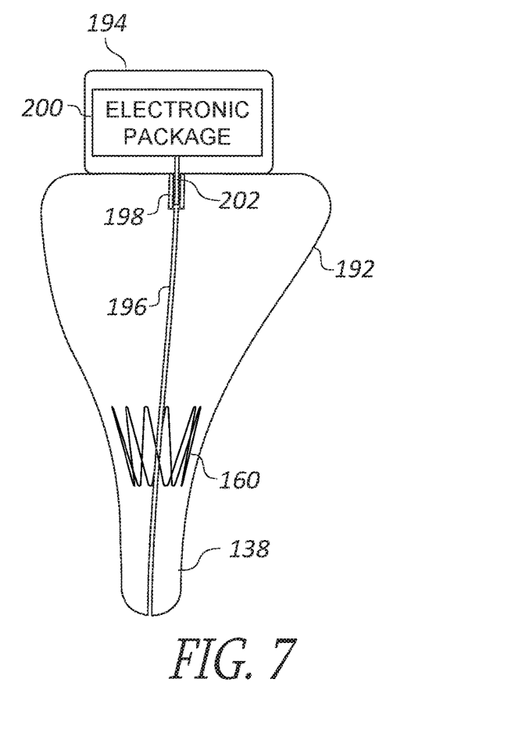

FIG. 7 is a diagrammatic side elevation view of an earplug 190, according to another embodiment. The earplug 190 includes a body 192 and a cap 194. The body 192 includes an audio transmission tube 196 extending the length of the body. A connector 198 is provided at the top of the tube 196 (as viewed in the drawings), and is made of an elastomeric plastic material. The cap 194 includes an electronic package 200 and an audio output tube 202. The audio transmission tube 196 is configured to be sufficiently flexible as to bend with the body 192 in the elbow region 120 of the ear canal 110, but also sufficiently rigid as to resist collapsing as it bends. The audio output tube 202 is a rigid plastic or metal, and is sized to fit within the connector 202 with a tight interference fit. The cap 194 is configured to be attached to the body 192 by the connection of the audio output tube 202 of the cap and the connector 198 of the body. According to an alternative embodiment, the output tube 202 is threaded, and is configured to engage threads formed in the connector 198. When in use, audio signals produced by the electronic package 200 are transmitted, via the audio output tube 198 and the audio transmission tube 196, to the horizontal canal 116 and the tympanum 108. Operation of the electronic package will be described below with reference to FIG. 9.

Figure 8:
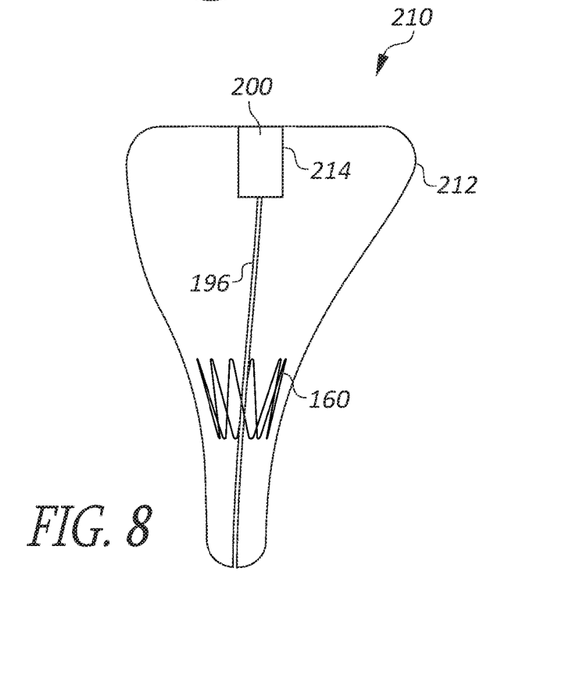

Turning now to FIG. 8, a diagrammatic side elevation view of an earplug 210 is provided, according to another embodiment. The earplug 210 includes a body 212 with a cavity 214 in which an electronic package 200 is positioned. The earplug 210 is similar in function to the earplug 190, but has the electronic package 200 positioned within the body, rather than in a cap, as described with referenced to the earplug 190 of FIG. 7.

Figure 9:
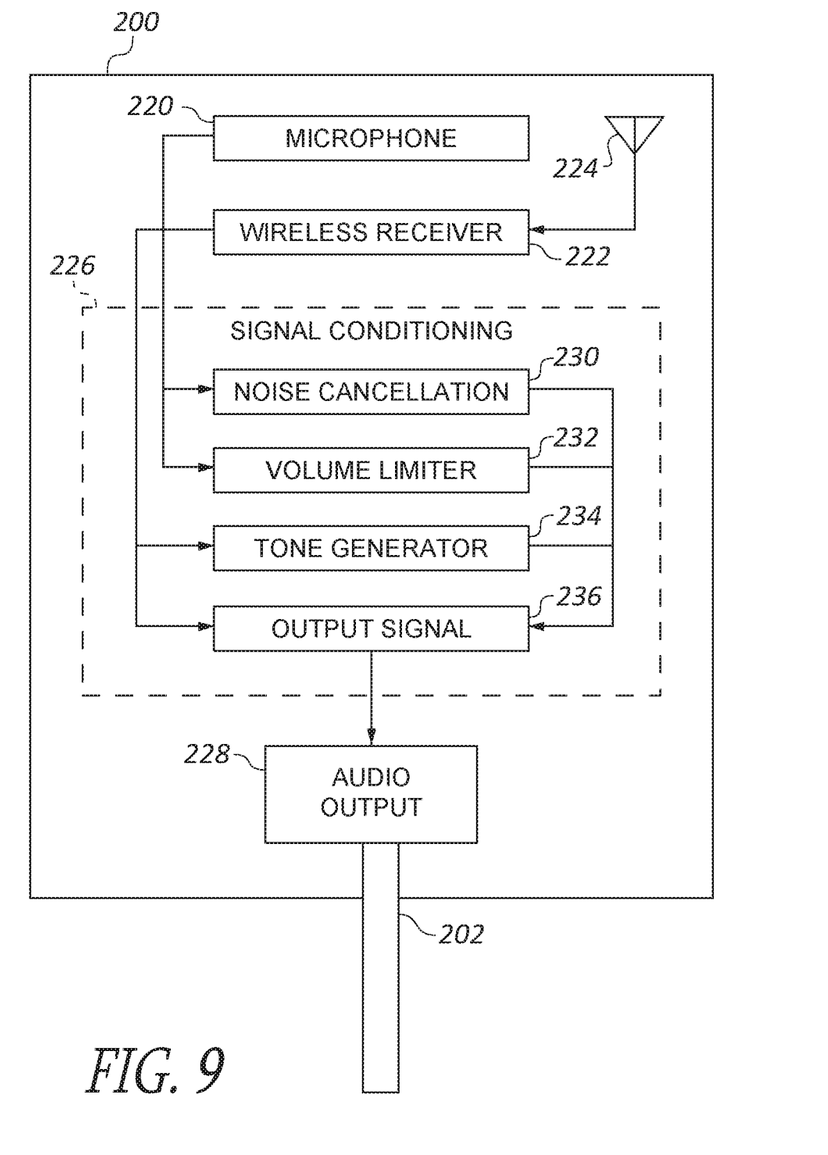
FIG. 9 is a schematic diagram of an electronic package for use with other embodiments, such as, e.g., one of the embodiments described with reference to FIG. 7 or 8, according to an embodiment.

FIG. 9 is a schematic diagram of an electronic package 200 for use with another embodiment, such as, e.g., one of the embodiments described with reference to FIG. 7 or 8, according to an embodiment. The electronic package 200 includes a number of components, including a microphone 220, a wireless receiver 222 and antenna 224, a signal conditioning module 226, and an audio output circuit 228. Some components that are not necessary for an understanding of the device are not shown in detail, such as a battery and power regulator, etc. The signal conditioning module 224 includes a noise cancellation circuit 230, a volume limiter circuit 232, a tone generator circuit 234, and an audio output signal generator circuit 236, which is connected to the audio output tube 202.

Operation of components of the electronic package 200 IS as follows: The microphone 220 is configured to receive ambient audio input and to transmit a corresponding input signal to the noise cancellation circuit 230 and/or the volume limiter circuit 232. The noise cancellation circuit 230 is configured to detect continuous or repetitive sounds and to produce a cancellation signal, which can be, for example, a signal that mirrors the detected sounds with a 180° phase relationship, and transmit the cancellation signal to the audio output signal generator 236. The volume limiter circuit 232 is configured to produce a volume limited signal that corresponds to ambient sounds, but in which the volume is limited to a level not exceeding an output volume threshold, so that very loud sounds, or sounds that exceed a high input threshold level, are reproduced at a lower volume. According to another embodiment, the volume limiter circuit 232 is configured to compress the ambient sounds, such that volume distribution in the volume limited signal is within a narrowed range that does not exceed the output volume threshold. According to a further embodiment, the volume limiter circuit 232 is also configured to amplify sounds that are below a low input threshold limit, or, in an embodiment that includes volume compression, to amplify very low-volume sounds to within the volume narrowed range.

The wireless receiver 222 is configured to receive a radio-frequency (RF) signal via the antenna 224, and to transmit a corresponding wireless input signal to the tone generator circuit 234 and/or directly to the output signal generator circuit 236. The tone generator circuit 234 is configured to produce one or more tone, click, or beep signals etc., in response to detected characteristics of the wireless input signal, and to transmit the signal to the audio output signal generator circuit 236. Alternatively, the wireless receiver 222 can be configured to detect the characteristics of the RF signal and to produce a command signal in response to which the tone generator circuit 234 produces and transmits the appropriate signal. According to an embodiment, the wireless receiver 222 is configured to convert the received RF signal to an audio-frequency signal, which it then transmits to the audio output signal generator circuit 236.

The audio output signal generator circuit 236 is configured to receive an input signal, and to generate and output a corresponding audio output signal via the audio output tube 202.

In practice, the components included in the electronic package 200, and their operation, will vary according to the intended use. For example, according to an embodiment, the electronic package 200 is included in an earplug that is intended to reduce distress that some dogs experience during airplane flights. In such an embodiment, the package 200 may include only the microphone 220, the noise cancellation circuit 230, the audio output signal generator circuit 236, and the audio output circuit 228.

According to another embodiment, the electronic package 200 is included in an earplug configured for use with a police dog. The Handler carries a radio transmitter configured to transmit voice commands. The electronic package 200, in that embodiment, includes the wireless receiver 222 and antenna 224, the audio output signal generator circuit 236, and the audio output circuit 228. The handler is able to transmit voice commands to direct the work of the dog, without the need to shout, which could be dangerous or counterproductive in certain circumstances. An embodiment intended for use with an animal trained to perform search-and-rescue operations might include the microphone 220, the wireless receiver 222 and antenna 224, the volume limiter circuit 232 configured to amplify very low-volume sounds, the audio output signal generator circuit 236, and the audio output circuit 228. With this configuration, the dog is able to receive voice commands from a handler and is protected from loud or distracting noises, at the same time having very small sounds amplified, which may improve the ability of the dog to locate victims buried under rubble or snow.

Many handlers do not use voice commands, but instead use hand-held clickers to produce sequences of clicks to train and/or direct the work of an animal. Other handlers use whistle signals or other sounds for the same purpose. The tone generator circuit 234 may be configured to produce the appropriate type of click, whistle, tone, etc., in response to a signal transmitted by the handler, in order to provide commands in the appropriate format for the animal. There are many other contemplated applications, each of which will suggest an appropriate combination of components. Furthermore, a person of ordinary skill in the art may find expanded capacities and training methods that are possible through the application of principles disclosed herein, that were not previously practical or even possible, but that might now offer significant new benefits. Such new embodiments are within the scope of the present disclosure and claims.

In the description of the embodiment of FIG. 9, various circuits and modules are described as separate elements, for clarity of description. However, these elements can be combined or separated into more or fewer elements that nevertheless perform the defined functions, or they can be combined with other devices that perform other functions in addition to those described here. To the extent that a system includes a structure or combination of structures that perform all of the functions recited in a claim, the claim reads on that system, at least with respect to those functions, even if the structures of the system cannot be easily separated into individual devices, each performing exactly the functions of a corresponding device of the claim. Likewise, a system that includes a processor configured to execute software instructions, in combination with such structures as would be necessary to perform the recited functions, and a memory device in which instructions for the performance of the recited functions are stored, is also within the scope of such a claim.

The inventor also contemplates embodiments in which mechanical elements are provided to perform one or more of the functions described above. For example, according to respective embodiments, the electronic package 200 of FIGS. 8 and 9, is replaced by a device configured to mechanically limit the volume of sound that passes down the audio transmission tube 196, thereby performing the function of the volume limiter circuit 232, as well as other associated elements. Such a device can, for example, include an intervening diaphragm whose deflection is controlled to within selected limits. Sound is transmitted by deflection of the diaphragm, to produce a corresponding pressure wave downstream. Sounds that do not reach or exceed a selected threshold are passed without significant attenuation, but because action of the diaphragm is controlled to prevent deflection beyond the selected threshold, sounds that do exceed the threshold are damped to an acceptable volume.

Figures 10A, 10B:
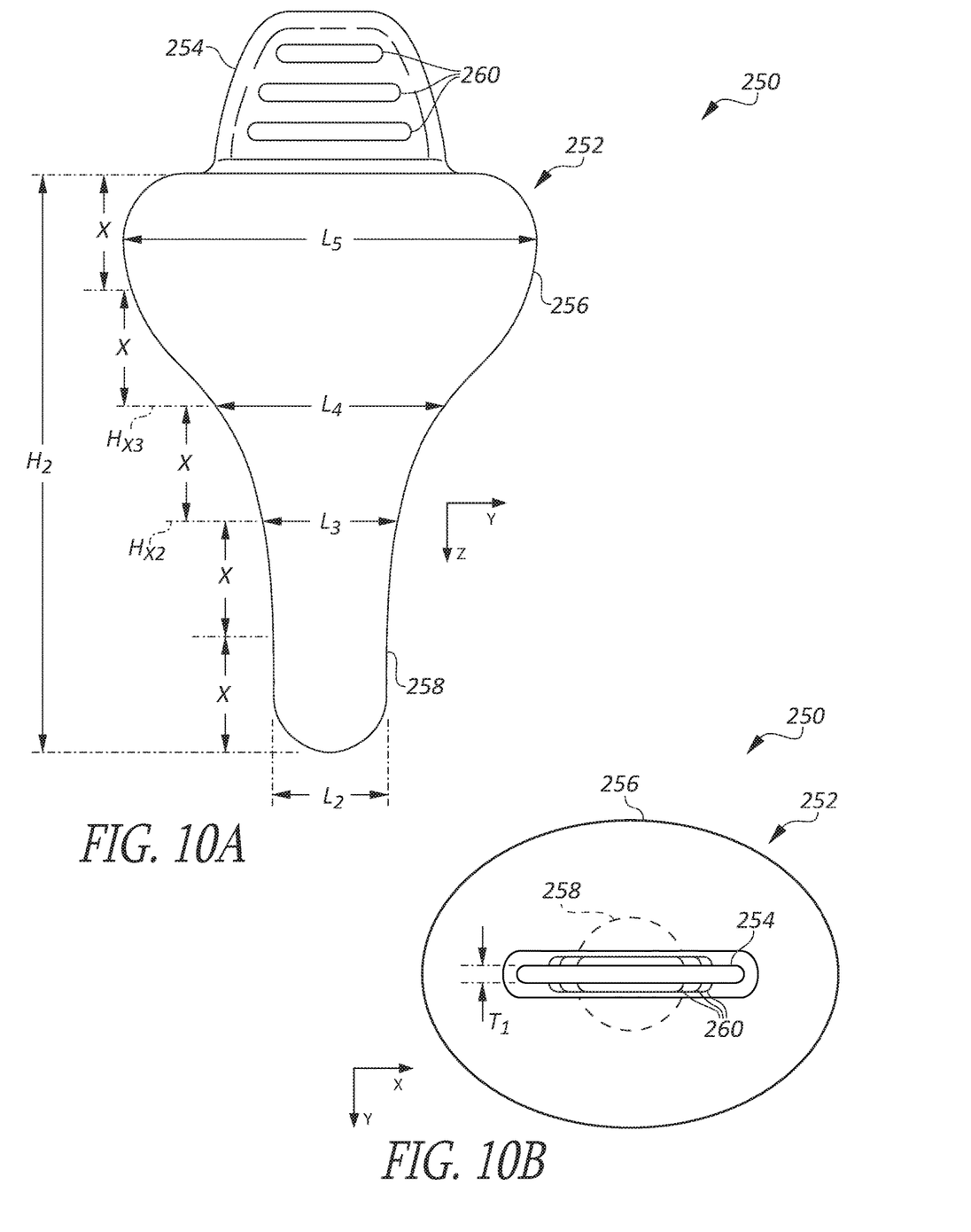
FIG. 10A is a side elevation view of an earplug for use in providing hearing protection for dogs and other animals, according to another embodiment.
FIG. 10B is a top plan view of the earplug of FIG. 10A.

FIG. 10A is a side elevation view of an earplug 250 for use in providing hearing protection for dogs and other animals, according to another embodiment, and FIG. 10B is a top plan view of the earplug 250 of FIG. 10A. The earplug 250 is similar in many respects to earplugs of other embodiments. Accordingly, the description that follows will be directed primarily to aspects in which the earplug 250 differs from other embodiments.

The earplug 250 includes a body 252 and a tab 254. The body 252 includes a first portion 256 and a second portion 258. The lowermost end of the second portion 258, as viewed in FIG. 10A, is shown in hidden lines in the plan view of FIG. 10B. The tab 254 includes a plurality of ridges 260.

The inventor has found that five different sizes are sufficient to accommodate the different ear sizes of a large majority of dogs. Inasmuch as the shape of the outer ear remains at least generally the same for dogs of different sizes, varying primarily in scale, the relative dimensions of the elements of the earplug 250 remain substantially constant among the different sizes. The tab, however, is sized to be grasped by an adult human, and so does not scale according to the size of the earplug, but remains substantially the same, except that, in the smallest sizes of earplugs, the length of the tab is reduced to fit the length of the smaller plugs.

According to an embodiment, the body 252 and tab 254 are formed of a same elastomeric material in a casting process. The inventor found that if the tab 254 is too stiff, it interferes with the pinna of a dog, at least in breeds that are 'flop-eared,' and that many dogs find this to be uncomfortable or distracting. Accordingly, a thickness T1 of the tab 254 can be selected to provide a degree of flexibility that permits the tab to flex easily, so as to be worn without discomfort by a dog with long ears. The thickness can vary, depending upon the particular material used, and may depend, for example, upon the elasticity and density of the material. The ridges 260 are configured, in size and shape, to enable a firm grip of the tab 254 between a handler's thumb and forefinger, to permit easy removal of the earplug 250 from a dog's ear canal.

As with embodiments described above, the first portion 256 of the body 252 has an oval shape, in plan view, but in this embodiment, the body 252 is bilaterally symmetrical, as seen in a side elevational view. This simplifies and speeds insertion, inasmuch as it is not necessary for the handler to remember how to orient the earplug for insertion, nor to determine which part of the earplug is the front or back. Characteristics of the material used in manufacturing the earplug are selected to be sufficiently conformable as to obviate the need for the bulge described with reference to the embodiment of FIGS. 2A-2C. The inventor contemplates other embodiments in which the first portion is substantially round, in plan view, and in which the material is selected so as conform to a dog's vertical ear canal regardless of the radial orientation of the device.

As the body 252 of the earplug 250 tapers, from its longest and widest dimensions near the upper end of the first portion 260, as viewed in FIG. 10A, toward the second portion, its lateral cross section transitions from an oval to a substantially round shape, as shown in hidden lines in FIG. 10B. The lower portion 238 has a length (and diameter) $L_2$ equal to a value X at or near the lowermost end of the second portion 258. Moving upward from the lowermost end, as viewed on FIG. 10A, the second portion 258 tapers only slightly, so that, at a height $H_{x2}$ (i.e., a height of about 2x) above the bottom of the second portion 258, the body 252 has a length $L_3$ less than about 25% (1.25x) greater than the value X. Between the height $H_{x2}$ and a height $H_{x3}$ the taper increases, so that at the height $H_{x3}$, a length $L_4$ of the body is between about 1.9 and 2.25 times the value X. The body 252 continues to taper out to its longest dimension, near a topmost end of the body, at which the length $L_5$ is between about 3.5 and 4 times the value X. Overall, the height H2 of the body 252 is between about 4.75 and 5.5 times the value X.

As used in the claims to define a position relative to a feature of a body of an earplug, the term near defines a distance that is within about 10% of the total height of the earplug body from the referenced feature. Thus, for example, referring to the embodiment shown in FIG. 10A, the longest transverse dimension of the body 252, length $L_5$, is at a height that is near the topmost end of the body, i.e., within about 10% of the total height of the body from its topmost end.

In the embodiment shown, the value X is equal to about 0.333 inches, the height H2 of the body 252 is about 1.72 inches, and the length Ls is equal to about 1.25 inches. The tab 234 is about 1;2 inch high and about % inch long. The thickness, i.e., width, of the tab 234 is about 0.12 inches. According to various embodiments, the thickness of the tab is between about 0.08 inch and about 0.25 inches. According to an embodiment, the earplug 250 is made of viscoelastic polyurethane foam, with a resiliency selected to enable the earplug 250 to return to its uncompressed shape in about eight seconds, from compression sufficient to fully insert the earplug into the ear canal of a dog of an appropriate size. According to other embodiments, the resiliency is selected to enable the earplug 250 to return to its uncompressed shape in between about five seconds and about fifteen seconds, from compression sufficient to fully insert the earplug into the ear canal of a dog of an appropriate size.

During the manufacturing process, in which the elastomeric material is injected—as a liquid—into a die to form the earplug 250, the material typically forms a smooth skin. According to an embodiment, prior to use, the inner surfaces of the die are subjected to an etching process that produces a slightly roughened texture on the surfaces. During the casting process, the texture of the die is transferred to the skin of the earplug 250, imparting a "tooth," or matte surface to the skin of the earplugs. It is believed that this surface texture aids in preventing the earplug 250 from falling from an animal's ear.

The inventor has found that earplugs are occasionally ingested by the animals for which they are intended. For the most part, this is not a particular problem, inasmuch as most kinds of materials that might be used to make the earplugs are not toxic to most animals, at least after the materials have cured, and the earplugs tend to pass through the animal with little difficulty. However, in the case of embodiments that are likely to be more expensive, such as those that include an electronic package, etc., it might be beneficial to be able to confirm that an earplug has been ingested. Accordingly, an embodiment is contemplated in which the material of the earplug is formulated to be radiopaque, and therefore easily detectable by a medical scan such as x-ray, etc.

Ordinal numbers, e.g., first, second, third, etc., are used in the claims according to conventional claim practice, i.e., for the purpose of clearly distinguishing between claimed elements or features thereof, etc. Ordinal numbers may be assigned arbitrarily, or assigned simply in the order in which elements are introduced. The use of such numbers does not suggest any other relationship, such as order of operation, relative position of such elements, etc. Furthermore, an ordinal number used to refer to an element in a claim should not be assumed to correlate to a number used in the specification to refer to an element of a disclosed embodiment on which that claim reads, nor to numbers used in unrelated claims to designate similar elements or features.

The abstract of the present disclosure is provided as a brief outline of some of the principles of the invention according to one embodiment, but is not intended as a complete or definitive description of any single embodiment thereof, nor should it be relied upon to define terms used in the specification or claims. The abstract does not limit the scope of the claims.

Reference throughout this specification to "one embodiment" or "an embodiment," and variations, indicates that a particular feature, structure, or characteristic described in connection with the embodiment is included in at least one embodiment. Thus, phrases such as "in one embodiment" or "according to an embodiment," as used in various places throughout this specification do not necessarily all refer to the same embodiment, nor do they suggest that the features described are limited to any single embodiment. Rather, individual features, structures, or characteristics described with reference to various separate embodiments can be combined in any suitable manner to form additional embodiments. The scope of the claims is therefore not limited by particular embodiments set forth herein, but should be construed in a manner consistent with the specification as a whole.

What is claimed is:

1. A device, comprising:
   an earplug body, of a resilient elastomeric material, having first and second ends and having a first transverse dimension near the first end, and a second transverse dimension near the second end, the second transverse dimension being at least 3.5 times the first transverse dimension, the body tapering from the first end toward the second end at a varying rate, such that at a point about 40 percent of a total length of the body from the first end, the body has a third transverse dimension of less than about 125 percent of the first transverse dimension, and at a point about 60 percent of the total length of the body from the first end, the body has a fourth transverse dimension of between about 190 percent and about 225 percent of the first transverse dimension; and
   a tab extending from the second end of the body and having a length and a height selected to facilitate grasping for removal of the device.

2. The device of claim 1, wherein the earplug body is formed of viscoelastic polyurethane.

3. The device of claim 2, wherein the earplug body has a recovery time of between about five seconds and about fifteen seconds.

4. The device of claim 2, wherein the earplug body has a recovery time of between about seven seconds and about ten seconds.

5. The device of claim 1, comprising:
   a spring element encapsulated within the earplug body and configured to apply a spring bias radially outward from an axis extending a length of the earplug body.

6. The device of claim 5, wherein the spring element is of a shape memory alloy having a transition temperature that is below the normal body temperature of a dog.

7. The device of claim 5, comprising an electronic package configured to produce a signal that is audible to an animal wearing the earplug.

8. The device of claim 1, wherein the total length of the earplug body is between about 4.5 and 5.5 times the first transverse dimension.

9. The device of claim 1, wherein the earplug body has an oval shape, in transverse cross-section near the second end.

10. The device of claim 1, wherein the earplug body is round in shape, in transverse cross-section near the first end.

11. The device of claim 1, wherein the tab is formed integrally with the earplug body in a molding process.

12. The device of claim 1, wherein the tab has a length of about 0.75 inches and a height of about 0.5 inches.

13. The device of claim 1, wherein the tab has a thickness of between about 0.08 and 0.12 inches.

14. The device of claim 1, wherein the material of the earplug body is radiopaque.

15. The device of claim 1, wherein the earplug body is bilaterally symmetrical, as seen in a side elevational view.

* * * * *